(12) United States Patent
Wang

(10) Patent No.: US 10,092,376 B2
(45) Date of Patent: Oct. 9, 2018

(54) ORTHODONTIC SELF-LOCKING BRACKET

(71) Applicant: Guangliang Wang, Hangzhou (CN)

(72) Inventor: Guangliang Wang, Hangzhou (CN)

(*) Notice: Subject to any disclaimer, the term of this patent is extended or adjusted under 35 U.S.C. 154(b) by 592 days.

(21) Appl. No.: 14/586,606

(22) Filed: Dec. 30, 2014

(65) Prior Publication Data

US 2015/0190213 A1 Jul. 9, 2015

(30) Foreign Application Priority Data

| Jan. 3, 2014 | (CN) | 2014 1 0013451 |
| Jan. 3, 2014 | (CN) | 2014 2 0017518 U |
| Mar. 24, 2014 | (CN) | 2014 1 0121283 |
| Mar. 24, 2014 | (CN) | 2014 1 0121284 |
| Jul. 10, 2014 | (CN) | 2014 1 0344506 |
| Nov. 10, 2014 | (CN) | 2014 1 0670875 |

(51) Int. Cl.
*A61C 7/28* (2006.01)
*A61C 7/34* (2006.01)
*A61C 7/30* (2006.01)

(52) U.S. Cl.
CPC ............. *A61C 7/287* (2013.01); *A61C 7/30* (2013.01); *A61C 7/34* (2013.01)

(58) Field of Classification Search
CPC ............. A61C 7/287; A61C 7/30; A61C 7/34
USPC ........................................................... 433/11
See application file for complete search history.

(56) References Cited

U.S. PATENT DOCUMENTS

| 7,828,549 | B1* | 11/2010 | Wildman | A61C 7/285 |
| | | | | 433/10 |
| 2004/0072117 | A1* | 4/2004 | Farzin-Nia | A61C 7/20 |
| | | | | 433/10 |
| 2006/0019212 | A1* | 1/2006 | Macchi | A61C 7/14 |
| | | | | 433/14 |
| 2006/0154196 | A1* | 7/2006 | Oda | A61C 7/287 |
| | | | | 433/13 |
| 2009/0155734 | A1* | 6/2009 | Damon | A61C 7/287 |
| | | | | 433/10 |
| 2009/0170049 | A1* | 7/2009 | Heiser | A61C 7/285 |
| | | | | 433/11 |
| 2010/0055636 | A1* | 3/2010 | Yeh | A61C 7/30 |
| | | | | 433/10 |
| 2010/0203463 | A1* | 8/2010 | Huff | A61C 7/287 |
| | | | | 433/10 |
| 2010/0285421 | A1* | 11/2010 | Heiser | A61C 7/285 |
| | | | | 433/11 |

(Continued)

*Primary Examiner* — Nicholas Lucchesi
(74) *Attorney, Agent, or Firm* — Jiwen Chen

(57) ABSTRACT

An orthodontic self-locking bracket includes a bracket body having an arch wire bracket slot and a bracket cover matched with the bracket body. Two sides of the arch wire bracket slot are provided with work wings. A bracket opening is arranged at the intersection of the arch wire bracket slot on the bracket body, and the bracket cover is inserted into the bracket opening and is in sliding fit with the bracket body. Left side of the arch wire bracket slot is provided with a pin shaft penetrating through the bracket opening, and the pin shaft is in clamping fit with the lower part of the bracket cover, so that the arch wire bracket slot can be closed and opened by the bracket cover. The bracket is locked and unlocked only by sliding rather than overturning the bracket cover. Complex operation for ligaturing a steel wire is eliminated.

18 Claims, 10 Drawing Sheets

(56) References Cited

U.S. PATENT DOCUMENTS

2012/0064476 A1\* 3/2012 Sabilla ............. A61C 7/28
433/11
2013/0224676 A1\* 8/2013 Alauddin ............ C22F 1/183
433/3

\* cited by examiner

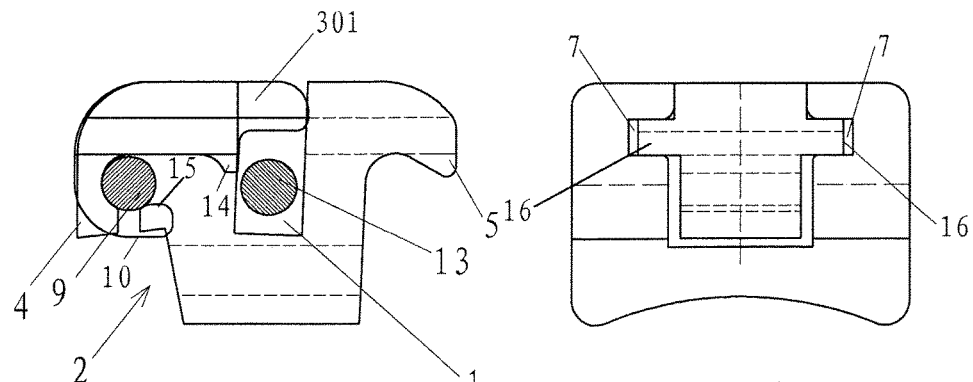
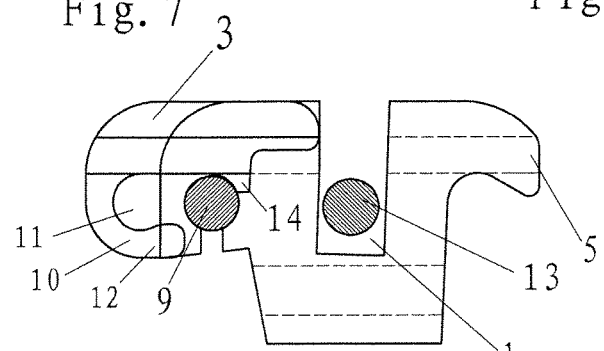
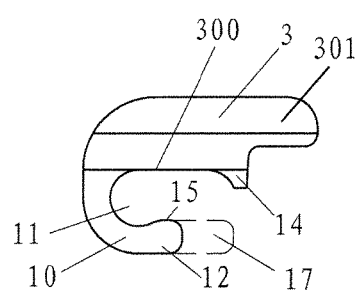
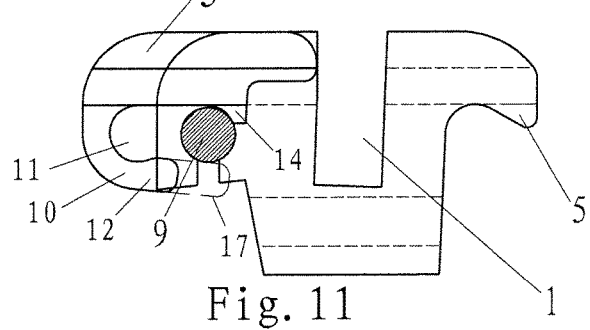
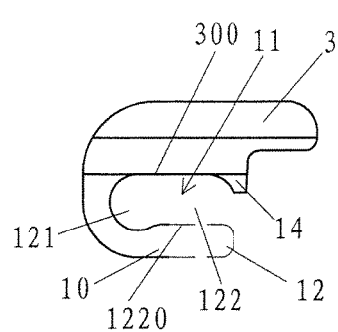
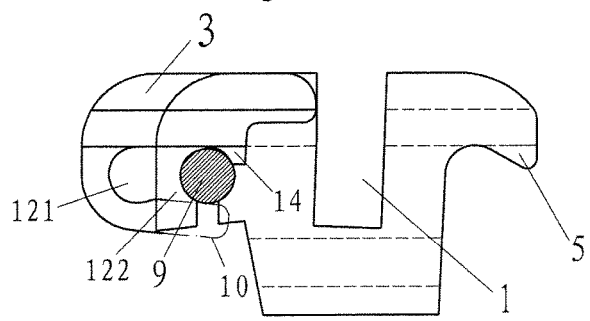

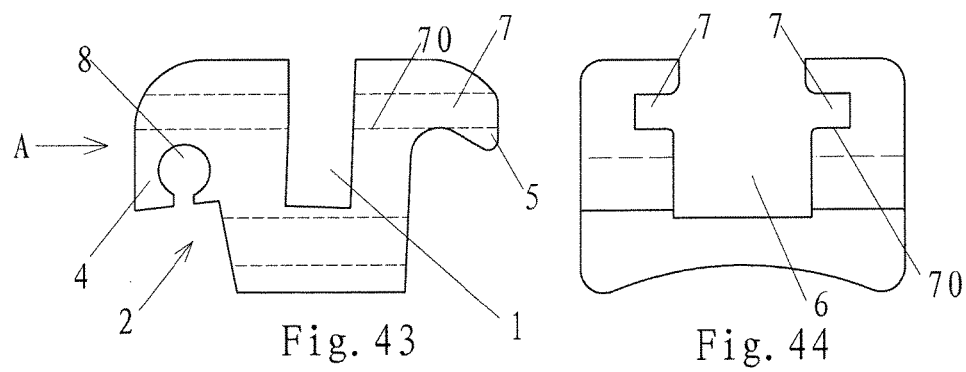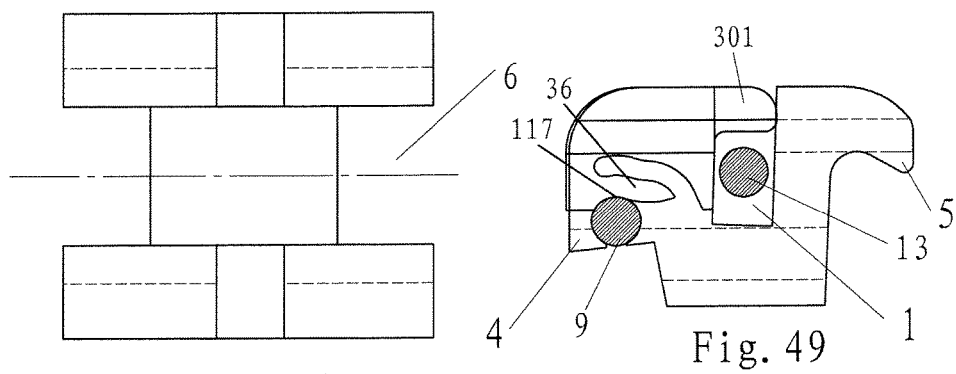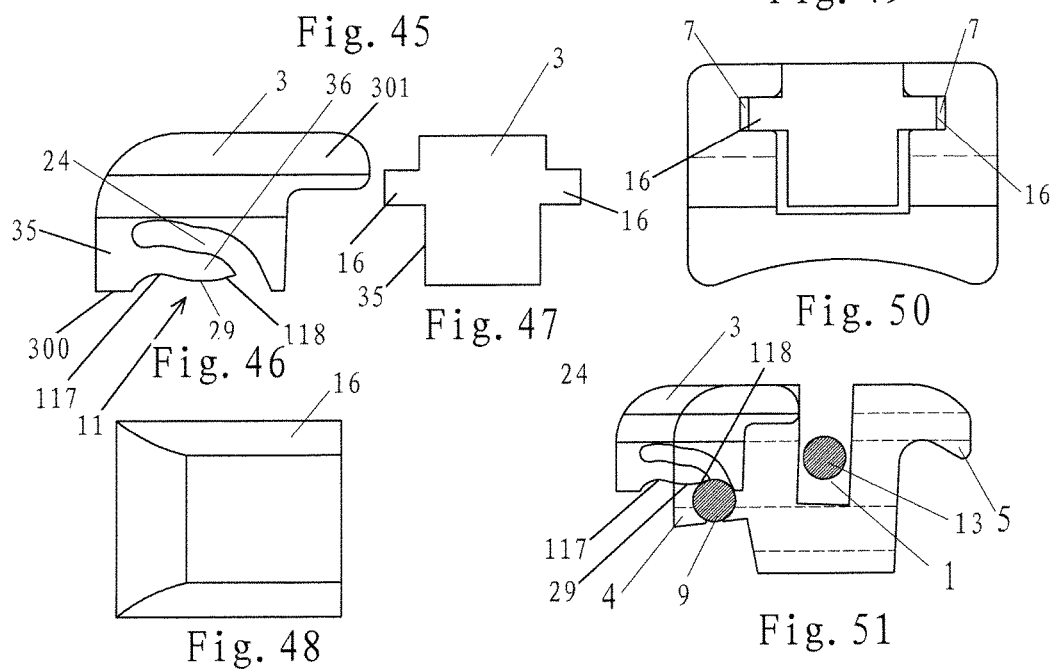

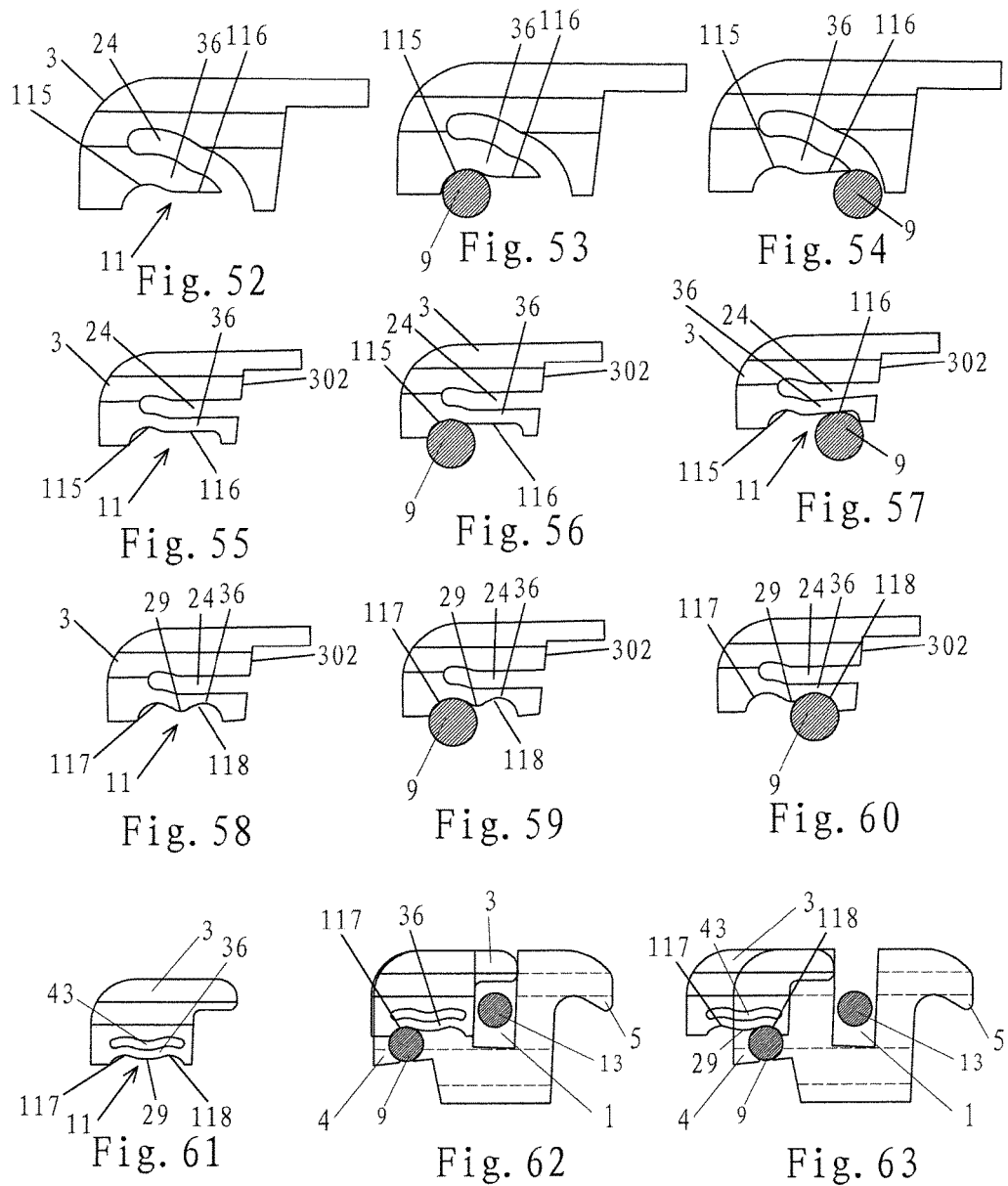

ORTHODONTIC SELF-LOCKING BRACKET

The present application claims the priorities of Chinese Patent Application No. 201410013451.9 filed Jan. 3, 2014, Chinese Patent Application No. 201420017518.1 filed Jan. 3, 2014, Chinese Patent Application No. 201410121284.X filed Mar. 24, 2014, Chinese Patent Application No. 201410121283.5 filed Mar. 24, 2014, Chinese Patent Application No. 201410344506.4 filed Jul. 10, 2014, and Chinese Patent Application No. 201410670875.2 filed Nov. 10, 2014, under 35 U.S.C. § 119, which are hereby incorporated by reference.

FIELD OF THE INVENTION

The present invention relates to the technical field of dental orthodontics, in particular to an orthodontic self-locking bracket.

BACKGROUND OF THE INVENTION

In the prior art, during the orthodontics, an orthodontic bracket is fixedly arranged on the dental face, an arch wire penetrates through an arch wire slot (a square wire slot) on the bracket, the arch wire is directly ligatured into the arch wire slot of the bracket by a ligature rubber ring or a ligature steel wire, and the orthodontic force of the arch wire transfers to the tooth through the bracket, so that the tooth can move prospectively, and the aim of the orthodontics can be achieved.

The ligature rubber ring or the ligature steel wire in the prior art is ligatured onto a ligature wing of the bracket, the force is directly applied onto the arch wire, the higher pressure is applied onto the arch wire, and the normal movement of the arch wire is baffled, so that the orthodontic effect of the tooth can be influenced. At present, there are various self-locking brackets on the market, having two major series such as the active type and the passive type, however, the self-locking brackets are complex in structure, difficult to manufacture, high in cost, expensive in price, and hard to operate.

SUMMARY OF THE INVENTION

Aiming at the defects in the prior art, the present invention provides an orthodontic self-locking bracket which is convenient to manufacture, simple to operate, stable and reliable.

The technical solution of the present invention is realized as follows:

An orthodontic self-locking bracket, comprising a bracket body having an arch wire bracket slot and a bracket cover matched with the bracket body, wherein two sides of the arch wire bracket slot are provided with work wings, a bracket opening is arranged at the intersection of the arch wire bracket slot on the bracket body, and the bracket cover is inserted into the bracket opening and is in sliding fit with the bracket body; the left side of the arch wire bracket slot is provided with a pin shaft penetrating through the bracket opening, and the pin shaft is in clamping fit with the lower part of the bracket cover, so that the arch wire bracket slot can be closed and opened by the bracket cover.

Preferably, two sides of the bracket opening are symmetrically provided with the sliding chute respectively, and the bracket cover is arranged within the sliding chutes.

Preferably, the sliding chutes arranged at two sides of the bracket opening are integrated into a dovetail groove, the longitudinal section of the bracket cover has the shape of swallow tail, and two sides of the bracket cover are clamped into the sliding chutes and slide along therewith. The sliding chutes are designed into the dovetail groove, and the shape and the size of the bracket cover are matched with those of the sliding chutes, so that the sliding chutes are simpler to manufacture and more smooth to slide.

Preferably, the sliding chutes arranged at two sides of the bracket opening are square chutes, two ends of the bracket cover are symmetrically provided with sliding blocks of which the shapes and the sizes are matched with the those of the square chutes, and the sliding blocks are clamped into the sliding chutes and slide along therewith. The square or rectangular sliding rails are convenient to machine and smooth in sliding fit.

Preferably, the upper part of the bracket cover covers on the work wing at the left side of the arch wire bracket slot, and a sliding rail face matched with the bracket cover is formed on the upper end of the work wing at the left side of the arch wire bracket slot. The space can be saved due to the structure design, so that the whole height of the bracket can be reduced. Meanwhile, the upper part of the bracket cover directly covers on the arch wire bracket slot and the work wing at the left side of the arch wire bracket slot, the upper surface of the bracket is integrated, a fractal line of the sliding chutes is unavailable, and the upper surface of the work wing at the right side of the arch wire bracket slot is level, so that the bracket is more clean and attractive in appearance integrally.

Preferably, the bracket cover has the shape of "I" integrally, two sides of the bracket cover are symmetrically provided with the concave sliding chutes, the bracket opening is narrow in the upper part and wide in the lower part, two sides of the upper part of the bracket opening are symmetrically provided with two sliding rails, after the bracket cover is inserted into the bracket opening, the sliding rails are in sliding fit with the sliding chutes, and the upper part of the bracket cover covers on the arch wire bracket slot and the work wing at the left side of the arch wire bracket slot.

Preferably, the bracket opening is a swallow-tail sliding chute integrally, the bracket cover comprises a bracket cover body and sliding blocks arranged under the bracket cover body to be matched with the swallow-tail sliding chute, after the bracket cover is inserted into the bracket opening, the sliding blocks are in sliding fit with the swallow-tail sliding chute, and the bracket cover body covers on the arch wire bracket slot and the work wing at the left side of the arch wire bracket slot.

Preferably, the bracket cover is provided with an elastic element which is deformable after being stressed, and a clamping slot which is in clamping fit with the pin shaft is arranged on the elastic element; the pin shaft makes the elastic element to be deformed and to be in clamping fit with the different positions of the clamping slot when the bracket cover slides, and the right end of the bracket cover covers or departs from the arch wire bracket slot. The pin shaft penetrates into the shaft hole always, the pin shaft is immovable relative to the bracket body, and the bracket cover slides within the sliding chute and is further in clamping fit with the pin shaft through the elastic element provided with the clamping slot, so that the bracket cover can be in clamping fit with the pin shaft at the different positions, and the bracket cover can be opened and locked.

The structure form of the elastic element has two solutions:

The first solution of the elastic element is as follows, preferably, the elastic element is a hook which is deformable after being stressed at one end of the bracket cover in a bending way, the hook is inserted into the bracket opening, and the hook is internally provided with the clamping slot; the bracket cover slides left and right, so that the right end of the bracket cover covers or departs from the arch wire bracket slot, and the hook is matched with the pin shaft, so that the bracket cover can be opened and closed. The clamping slot can be named as a hook slot of the hook, and the pin shaft is placed within the hook and matched with the hook.

Preferably, the clamping slot of the hook is an arc slot, the free end of the hook tilts to form into a lug boss which is in clamping fit with the pin shaft, the pin shaft is clamped into the clamping slot of the hook and is limited by the lug boss when the bracket cover is closed, the lug boss passes through the pin shaft and makes the hook to be deformed when the bracket cover is opened.

Preferably, the shape and the size of the clamping slot of the hook are matched with those of the cross section of the pin shaft; and the free end of the hook titles to form into the lug boss which is in clamping fit with the pin shaft.

Preferably, the hook is formed by the means that one end of the bracket cover is bent towards the bottom surface of the bracket cover at 180 degrees, the length of the hook is lengthened, so that the pin shaft can not slide out of the clamping slot, the clamping slot of the hook comprises an internal clamping slot which departs from the free end of the hook and an external clamping slot which is near to the free end of the hook, the shape and the size of the internal clamping slot are matched with those of the cross section of the pin shaft, and the height of the external clamping slot is less than the diameter of the pin shaft; the pin shaft is clamped into the internal clamping slot when the bracket cover is closed, and the pin shaft is arranged within the external clamping slot and makes the hook to be deformed when the bracket cover is opened. The height of the external clamping slot is the distance between the inner side face of the hook and the bottom surface of the bracket cover, and due to the technical solution, the length of the hook is properly lengthened, so that after the pin shaft departs from the internal clamping slot of the hook and enters into the external clamping slot, the pin shaft can be still arranged within the hook, therefore, when the bracket cover is closed, the resistance can be reduced, and the ideal object that the force is large to apply when the bracket cover is opened and the force is small to apply when the bracket cover is closed can be realized.

Preferably, the hook is slantwise arranged towards the bottom surface of the bracket cover, and the size of the clamping slot of the hook is gradually reduced from inside to outside; the pin shaft is clamped into the maximum space of the clamping slot when the bracket cover is closed, and the pin shaft is arranged at the place which is near to the free end of the hook and makes the hook to be deformed when the bracket cover is opened. Therefore, the pin shaft makes the bracket cover to be locked due to the elastic force of the bracket cover, and the bracket cover is easy to reset from being opened to being closed.

Preferably, an arc lug boss is arranged in the middle of the clamping slot of the hook, and the clamping slot is divided into a left clamping slot and a right slot, which can be in clamping fit with the pin shaft respectively, by the arc lug boss;

when the bracket cover is rightwards pushed, the pin shaft is clamped into the left clamping slot of the hook, the hook is positioned with the pin shaft through the arc lug boss in a clamping way, the right end of the bracket cover covers the arch wire bracket slot, and the bracket cover is locked in a closing way;

when the bracket cover is leftwards pushed, the pin shaft is clamped into the right clamping slot of the hook, and the right end of the bracket cover departs from the arch wire bracket slot as well, so that the arch wire bracket slot can be exposed, the arch wire can be taken in or out, and the bracket cover is opened.

Preferably, the clamping slot is divided into two sections, the left section is an arc slot, the right section is a straight slot, and the lowest point at the lower end of the pin shaft and the bottom of the arc slot are lower than the bottom of the straight slot;

When the bracket cover is rightwards pushed, the pin shaft is clamped into the arc slot, the right end of the bracket cover covers the arch wire bracket slot, and the bracket cover is locked in a closing way;

When the bracket cover is leftwards pushed, the pin shaft departs from the arc slot, enters into the straight slot, and makes the hook to be deformed, and the right end of the bracket cover departs from the arch wire bracket slot as well, so that the arch wire bracket slot can be exposed, the arch wire can be taken in or out, and the bracket cover is opened.

Preferably, a stop block used for stopping the pin shaft to prevent the bracket cover from sliding out of the bracket body is arranged on the bottom surface of the bracket cover, and the stop block is arranged within the bracket opening. Therefore, the bracket cover can not slide out of the bracket body when the bracket cover is opened.

Preferably, the part of the right end of the bracket cover, which is used for covering the arch wire bracket slot, is configured into a thin and flat cover body. Therefore, in the case that the arc wire placing space is guaranteed, the height of the bracket body can be reduced.

In order to make the whole bracket to be more attractive in appearance, based on the solution that the upper part of the bracket cover covers on the work wing at the left side of the arc wire bracket slot, preferably, the upper surface of the work wing at the left side of the arch wire bracket slot is lower than the upper surface of the work wing at the right side of the arch wire bracket slot, and when the upper part of the bracket cover covers on the work wing at the left side of the arch wire bracket slot, the upper surface of the bracket cover is in parallel with the upper surface of the work wing at the right side of the arch wire bracket slot.

The second solution of the elastic element is as follows:

Preferably, the clamping slot is concavely arranged on the bottom surface of the bracket cover, the elastic element is the shrapnel which is deformable after being stressed above the clamping slot, and the upper end of the pin shaft is arranged within the clamping slot and is in contacting fit with the shrapnel.

Preferably, the clamping slot is divided into two sections, the left section is the arc slot of which the bottom is arc, the right section is the straight slot of which the bottom is horizontal, the highest point of the arc slot is higher than the plane where the bottom of the straight slot is placed, and the height of the plane where the bottom of the straight slot is placed is lower than the highest point of the pin shaft; the bracket cover is internally provided with a gap, the start point of the gap is placed at the right end of the clamping slot, the end point of the gap is placed above the arc slot, and the shrapnel is formed at the part surrounded by the gap and the clamping slot;

When the bracket cover is rightwards pushed, the upper end of the pin shaft is clamped into the arc slot of the bracket cover, the right end of the bracket cover covers the arch wire bracket slot, and the bracket cover is locked in a closing way;

When the bracket cover is leftwards pushed, the arc slot of the bracket cover departs from the pin shaft, the pin shaft makes the shrapnel to be deformed and clamped into the straight slot of the bracket cover, and the right end of the bracket cover departs from the arch wire bracket slot as well, so that the arch wire bracket slot can be exposed, the arch wire can be taken in or out, and the bracket cover is opened.

Preferably, the clamping slot is an arc slot integrally, a flange downwards extends out of the middle of the arc slot, the lower end of the flange is higher than the bottom surface of the bracket cover, and the arc slot is divided into a left arc slot and a right arc slot, which can be in clamping fit with the pin shaft respectively, by the flange; the bracket cover is internally provided with a gap, the start end of the gap is placed at the right end of the clamping slot, the end point of the gap is placed above the left arc slot, and a shrapnel is formed at the part surrounded by the gap and the clamping slot; the lower end of the flange is higher than the bottom surface of the bracket cover, i.e. the lower end of the flange can not exceed the bottom surface of the bracket cover;

When the bracket cover is rightwards pushed, the upper end of the pin shaft is clamped into the left arc slot of the bracket cover, the right end of the bracket cover covers the arch wire bracket slot, and the bracket cover is locked in a closing way;

When the bracket cover is leftwards pushed, the arc slot of the bracket cover departs from the pin shaft, the pin shaft makes the shrapnel to be deformed and clamped into the right arc slot of the bracket cover, and the right end of the bracket cover departs from the arch wire bracket slot as well, so that the arch wire bracket slot can be exposed, the arch wire can be taken in or out, and the bracket cover is opened.

Preferably, from right to left, the gap is arranged upwards and slantwise.

Preferably, the bottom of the straight slot is arranged horizontally or slantwise.

Preferably, the clamping slot is divided into two sections, the left section is the arc slot of which the bottom is arc, the right section is the straight slot of which the bottom is horizontal, the highest point of the arc slot is higher than the plane where the bottom of the straight slot is placed, and the height of the plane where the bottom of the straight slot is placed is lower than the highest point of the pin shaft; the bracket cover is internally provided with a gap, the start point of the gap is placed on the right side face of the bracket cover, the end point of the gap is placed above the arc slot, and the shrapnel is formed between the gap and the clamping slot;

When the bracket cover is rightwards pushed, the upper end of the pin shaft is clamped into the arc slot of the bracket cover, the right end of the bracket cover covers the arch wire bracket slot, and the bracket cover is locked in a closing way;

When the bracket cover is leftwards pushed, the arc slot of the bracket cover departs from the pin shaft, the pin shaft makes the shrapnel to be deformed and clamped into the straight slot of the bracket cover, and the right end of the bracket cover departs from the arch wire bracket slot as well, so that the arch wire bracket slot can be exposed, the arch wire can be taken in or out, and the bracket cover is opened.

Preferably, the clamping slot is an arc slot integrally, a flange downwards extends out of the middle of the arc slot, the lower end of the flange is higher than the bottom surface of the bracket cover, and the arc slot is divided into a left arc slot and a right arc slot, which can be in clamping fit with the pin shaft respectively, by the flange; the bracket cover is internally provided with a gap, the start end of the gap is placed on the right side face of the bracket cover, the end point of the gap is placed above the arc slot, and a shrapnel is formed between the gap and the clamping slot;

When the bracket cover is rightwards pushed, the upper end of the pin shaft is clamped into the left arc slot of the bracket cover, the right end of the bracket cover covers the arch wire bracket slot, and the bracket cover is locked in a closing way;

When the bracket cover is leftwards pushed, the left arc slot of the bracket cover departs from the pin shaft, the pin shaft makes the shrapnel to be deformed and clamped into the right arc slot, and the right end of the bracket cover departs from the arch wire bracket slot as well, so that the arch wire bracket slot can be exposed, the arch wire can be taken in or out, and the bracket cover is opened.

In order to make the bracket cover to be smoother to slide, preferably, the flange is arc.

Preferably, the gap is linear, and the gap is in parallel with the bottom surface of the bracket cover basically.

Preferably, the clamping slot is an arc slot integrally, a flange downwards extends out of the middle of the arc slot, the lower end of the flange is higher than the bottom surface of the bracket cover, and the arc slot is divided into a left arc slot and a right arc slot, which can be in clamping fit with the pin shaft respectively, by the flange; the bracket cover is internally provided with a kidney hole, the kidney hole is arranged above the clamping slot, and a shrapnel is formed between the kidney hole and the clamping slot;

When the bracket cover is rightwards pushed, the upper end of the pin shaft is clamped into the left arc slot of the bracket cover, the right end of the bracket cover covers the arch wire bracket slot, and the bracket cover is locked in a closing way;

When the bracket cover is leftwards pushed, the left arc slot of the bracket cover departs from the pin shaft, the pin shaft makes the shrapnel to be deformed and clamped into the right arc slot, and the right end of the bracket cover departs from the arch wire bracket slot as well, so that the arch wire bracket slot can be exposed, the arch wire can be taken in or out, and the bracket cover is opened.

In order to make the shrapnel deformation to be more easily controlled, preferably, the shape of the kidney hole is matched with that of the bottom of the clamping slot.

Preferably, the lower part of the bracket cover is provided with a convex block, the convex block is inserted into a bracket opening, the bracket is arranged on the bottom surface of the convex block, and the shrapnel is arranged within the convex block. Therefore, the machining of the shrapnel is wider in machining range, the slide of the bracket cover and the deformation of the shrapnel can not be influenced with each other, and the height of the bracket body can be reduced.

Preferably, the part of the right end of the bracket cover, which is used for covering the arch wire bracket slot, is configured into a thin and flat cover body. Therefore, in the case that the arc wire placing space is guaranteed, the height of the bracket body can be reduced.

In order to make the whole bracket to be more attractive in appearance, preferably, a cover plate used for covering the bracket opening extends towards the middle of the bracket opening on the work wing at the right side of the arch wire bracket slot.

Preferably, the work wing at the right side of the arc wire bracket slot is provided with an auxiliary correcting hole through which an auxiliary arc wire can penetrate, and the auxiliary correcting hole is in parallel with the arc wire bracket slot. Therefore, the double arc wires can be formed, so that the bracket is better in correcting effect.

Preferably, the highest point of the pin shaft or the shaft hole is lower than the plane where the bottom of the sliding chute is placed. Therefore, the bracket can be installed more conveniently only by the means that the bracket cover is clamped into the sliding chutes, and the pin shaft is assembled.

The installing mode of the pin shaft is as follows: preferably, the work wing at the left side of the arch wire bracket slot is provided with a shaft hole, the shaft hole is intercrossed with the bracket opening and penetrates through the bracket body, and the pin shaft penetrates into the shaft hole and penetrates through the bracket opening.

INDUSTRIAL APPLICABILITY AND ADVANTAGEOUS EFFECTS

The present invention adopts the structure of a sliding lock plate, the bracket cover is inserted into the bracket opening and is in sliding fit with the bracket body, the work wing at the left side of the arc wire bracket slot is provided with the pin shaft, the pin shaft penetrates into the shaft hole always, the pin shaft is immovable relative to the bracket body, and the bracket cover slides within the sliding chute and is further in clamping fit with the pin shaft through the elastic element provided with the clamping slot, so that the bracket cover can be closed or opened.

Specifically, aiming at the match between the bracket cover and the bracket opening, the present invention provides two different structure forms, wherein one structure form is that two sides of the bracket opening are provided with the sliding chutes; and the other structure form is that the bracket cover covers on the upper surface of the work wing at the left side of the arc wire bracket slot, and the sliding chutes are arranged on the bracket cover.

Furthermore, aiming at the elastic element, the present invention further provides two different structure forms, one structure form is the hook form, the inner side face of the hook is provided with a clamping slot or a hook slot, and the bracket cover can be closed or opened due to the match between the hook and the pin under different conditions; when the bracket cover slides left and right, the pin shaft can be matched with the different positions of the hook within the clamping slot of the hook, or the pin shaft is clamped into or departs from the clamping slot of the hook, and the right end of the bracket can depart from or cover the arc wire bracket slot, so that the bracket cover is closed or opened; the other structure form is that the bottom of the bracket cover is cut with a shrapnel, and the clamping slot is placed on the bottom surface of the shrapnel, so that along with the slide of the bracket cover, the pin shaft makes the shrapnel to be deformed and clamped into the different positions of the clamping slot, and the right end of the bracket can cover or depart from the arc wire bracket slot, therefore, the bracket cover is closed or opened.

Generally, the bracket body and the bracket cover are easy to manufacture and can be formed at one time by means of linear cutting, so that the bracket is convenient to operate. Meanwhile, the bracket cover is placed within the bracket body, so that the bracket is less in volume. The bracket can be locked and unlocked only by sliding the bracket cover rather than overturning the bracket cover; in the clinical application, not only can the complex operation for ligaturing the steel wire be eliminated, but also the bracket can be conveniently operated.

BRIEF DESCRIPTION OF THE DRAWINGS

FIG. 7 is the schematic diagram of the close status of the bracket cover in embodiment 1;

FIG. 8 is the schematic diagram of the sliding fit status between the bracket cover and the sliding chutes in embodiment 1;

FIG. 9 is the schematic diagram of the open status of the bracket cover in embodiment 1;

FIG. 10 is the structure schematic diagram of the deformation 1 of the bracket cover in embodiment 1;

FIG. 11 is the schematic diagram of the open status of the deformation 1 of the bracket cover in embodiment 1;

FIG. 12 is the structure schematic diagram of the deformation 2 of the bracket cover in embodiment 1;

FIG. 13 is the schematic diagram of the open status of the deformation 2 of the bracket cover in embodiment 1;

FIG. 43 is the structure schematic diagram of the bracket body in embodiment 5;

FIG. 44 is the auxiliary view A of FIG. 43;

FIG. 45 is the top plan structure schematic diagram of FIG. 43;

FIG. 46 is the structure schematic diagram of the bracket cover in embodiment 5;

FIG. 47 is the side view of FIG. 46;

FIG. 48 is the structure schematic diagram of the vertical status of FIG. 46;

FIG. 49 is the schematic diagram of the close status of the bracket cover in embodiment 5;

FIG. 50 is the schematic diagram of the sliding fit status between the bracket cover and the sliding chutes in embodiment 5;

FIG. 51 is the schematic diagram of the open status of the bracket cover in embodiment 5;

FIG. 52 is the structure schematic diagram of the deformation 1 of the bracket cover in embodiment 5;

FIG. 53 is the schematic diagram of the match between the deformation 1 of the bracket cover and the pin shaft under the status that the bracket cover is closed in embodiment 5;

FIG. 54 is the schematic diagram of the match between the deformation 1 of the bracket cover and the pin shaft under the status that the bracket cover is opened in embodiment 5;

FIG. 55 is the structure schematic diagram of the deformation 2 of the bracket cover in embodiment 5;

FIG. 56 is the schematic diagram of the match between the deformation 2 of the bracket cover and the pin shaft under the status that the bracket cover is closed in embodiment 5;

FIG. 57 is the schematic diagram of the match between the deformation 2 of the bracket cover and the pin shaft under the status that the bracket cover is opened in embodiment 5;

FIG. 58 is the structure schematic diagram of the deformation 3 of the bracket cover in embodiment 5;

FIG. 59 is the schematic diagram of the match between the deformation 3 of the bracket cover and the pin shaft under the status that the bracket cover is closed in embodiment 5;

FIG. 60 is the schematic diagram of the match between the deformation 3 of the bracket cover and the pin shaft under the status that the bracket cover is opened in embodiment 5;

FIG. 61 is the structure schematic diagram of the deformation 4 of the bracket cover in embodiment 5;

FIG. 62 is the schematic diagram of the match between the deformation 4 of the bracket cover and the pin shaft under the status that the bracket cover is closed in embodiment 5;

FIG. 63 is the schematic diagram of the match between the deformation 4 of the bracket cover and the pin shaft under the status that the bracket cover is opened in embodiment 5;

DETAILED DESCRIPTION OF THE PREFERRED EMBODIMENTS

Figures 1, 2:
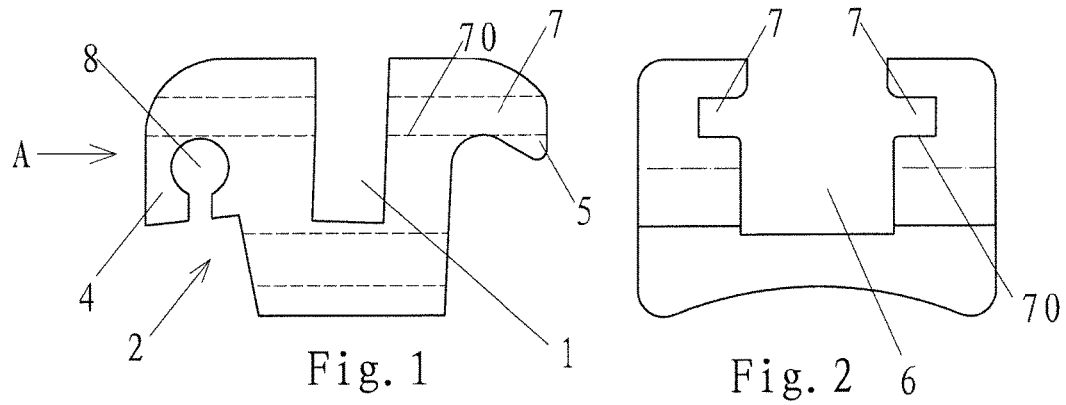
FIG. 1 is the structure schematic diagram of the bracket body in embodiment 1.
FIG. 2 is the auxiliary view A of FIG. 1.
Figure 3:
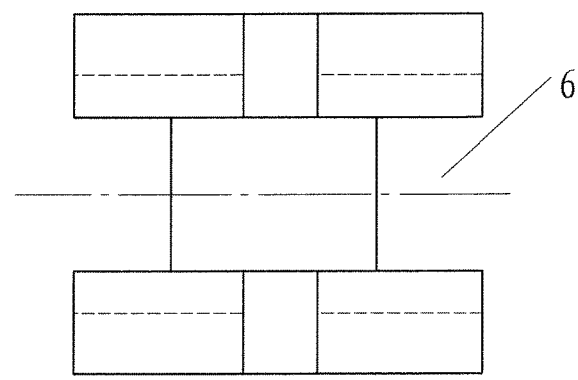
FIG. 3 is the top plan structure schematic diagram of FIG. 1.

The specific embodiments of the present invention are as follows:

Embodiment 1

An orthodontic self-locking bracket, as shown in FIG. 1-FIG. 9, comprising a bracket body 2 having an arch wire bracket slot 1 and a bracket cover 3 matched with the bracket body 2, wherein two sides of the arch wire bracket slot 1 are respectively provided with work wings 4 and 5, a bracket opening 6 is arranged at the intersection of the arch wire bracket slot 1 on the bracket body 2, two sides of the bracket opening 6 are symmetrically provided with a sliding chute 7 respectively formed by means of linear cutting, the bracket cover 3 is put into the sliding chutes 7 and slides along with the sliding chutes 7, the work wing 4 at the left side of the arch wire bracket slot 1 is provided with a shaft hole 8, the shaft hole 8 is intercrossed with the bracket opening 6 and penetrates through the bracket body 2, the shaft hole 8 is internally provided with a pin shaft 9 which penetrates through the bracket opening 6, and the upper end of the shaft hole 8 is not higher than the bottom surfaces 70 of the sliding chutes 7.

As shown in FIG. 2 and FIG. 8, the sliding chutes 7 at two sides of the bracket opening are the square chutes, two ends of the bracket cover 3 are symmetrically provided with sliding blocks 16 of which the shapes and the sizes are matched with the those of the square chutes, and the sliding blocks 16 are clamped into the sliding chutes 7 and slide along with the sliding chutes 7.

Figures 4, 5:
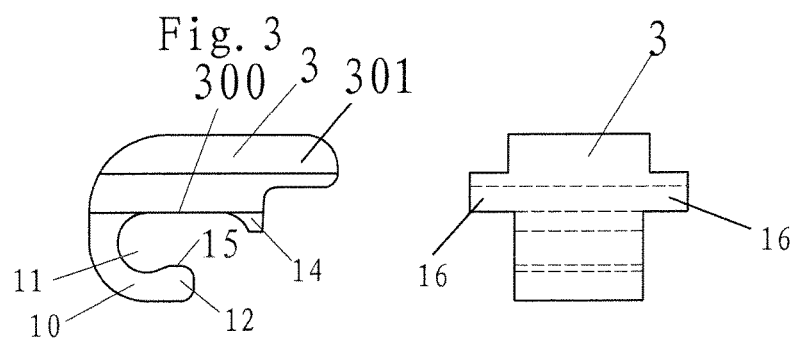
FIG. 4 is the structure schematic diagram of the bracket cover in embodiment 1.
FIG. 5 is the side view of FIG. 4.
Figure 6:
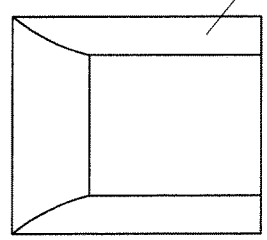
FIG. 6 is the top plan structure schematic diagram of FIG. 4.

As shown in FIG. 4, FIG. 5 and FIG. 6, the bracket cover 3 is provided with an elastic element which is in clamping fit with the pin shaft 9, the elastic element is a hook 10 which is deformable after being stressed at one end of the bracket cover 3 in a bending way, the hook 10 is inserted into the bracket opening 6, the hook 10 is internally provided with the clamping slot 11, the clamping slot 11 can be named as a hook slot as well, the clamping slot 11 is an arc slot matched with the pin shaft 9, the preferable mode is as follows: the shape and the size of the clamping slot 11 are matched with those of the cross section of the pin shaft 9; and a free end 12 of the hook 10 is provided with a lug boss 15 which is in clamping fit with the pin shaft 9.

Under the structure form of the embodiment, a stop block 14 used for stopping the pin shaft to prevent the bracket cover from sliding out of the bracket body is arranged in the middle of the bottom surface 300 of the bracket cover 3, and the stop block 14 is arranged within the bracket opening 6.

As shown in FIG. 7 and FIG. 8, when the bracket cover is rightwards pushed, the pin shaft 9 is clamped into the clamping slot 11, the hook is in positioned with the pin shaft 9 by the lug boss 15 in a clamping way, the right end of the bracket cover covers the arch wire bracket slot, and the bracket cover is locked in a closing way.

As shown in FIG. 9, when the bracket cover is leftwards pushed, the pin shaft 9 departs from the clamping slot 11, the lug boss 15 is stressed to make the hook 10 to be elastically deformed when passing through the pin shaft 9, the pin shaft 9 departs from the clamping slot 11 finally, meanwhile, the stop block 14 arranged at the bottom surface of the bracket cover 3 is stopped by the upper end of the pin shaft 9, and the right end of the bracket cover 3 departs from the arch wire bracket slot 1 as well, so that the arch wire bracket slot 1 can be exposed, the arch wire 13 can be taken in or out, and the bracket cover 3 is opened.

The part of the right end of the bracket cover 3, which is used for covering the arch wire bracket slot 1, is configured into a thin and flat cover body 301, so that the arc wire placing space can enlarged, and the height of the bracket body can be reduced.

The deformation 1 of the bracket cover in embodiment 1: as the improvement of the bracket cover in embodiment 1, the hook 10 is lengthened to prevent the pin shaft 9 from departing from the hook 10 at the beginning design time; as shown in FIG. 10 and FIG. 11, the deformation 1 of the bracket cover is that an extension section 17 extends out of the free end 12 of the hook 10 outwards and horizontally, the width of the extension section 17 can be less than that of the hook 10, and the inner side face of the extension section 17, i.e. the side facing to the bottom surface 300 of the bracket cover, is in parallel with the upper end face of the lug boss 15, so that after the pin shaft 9 departs from the clamping slot 11 of the hook 10, the pin shaft 9 can be still placed within the hook 10, therefore, when the bracket cover 3 is closed again, the resistance can be reduced, and the ideal object that the force is large to apply when the bracket cover is opened and the force is small to apply when the bracket cover is closed can be realized.

The deformation 2 of embodiment 1: being similar to the deformation 1: as shown in FIG. 12 and FIG. 13, the hook 10 is formed by the means that one end of the bracket cover is bent towards the bottom surface of the bracket cover at 180 degrees, the length of the hook 10 is lengthened, so that the pin shaft 9 can not slide out of the clamping slot, the free end 12 of the hook 10 is placed at the end of the hook, the clamping slot 11 of the hook comprises an internal clamping slot 121 which departs from the free end 12 of the hook and an external clamping slot 122 which is near to the free end 12 of the hook, the shape and the size of the internal clamping slot 121 are matched with those of the cross section of the pin shaft 9, and the height of the external clamping slot 122, i.e. the distance between the lower end face 1220 of the external clamping slot and the bottom surface 300 of the bracket cover, is less than the diameter of the pin shaft 9 or the lower end face 1220 of the external clamping slot 122 is higher than the lower end of the pin shaft 9; the pin shaft is clamped into the internal clamping slot when the bracket cover is closed, and the pin shaft is arranged within the external clamping slot and makes the hook to be deformed when the bracket cover is opened.

Figure 14:
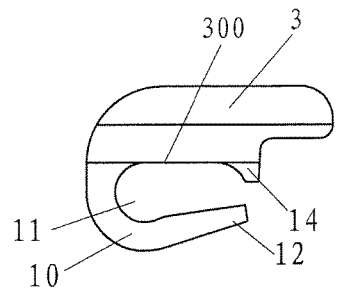
FIG. 14 is the structure schematic diagram of the deformation 3 of the bracket cover in embodiment 1.
Figure 15:
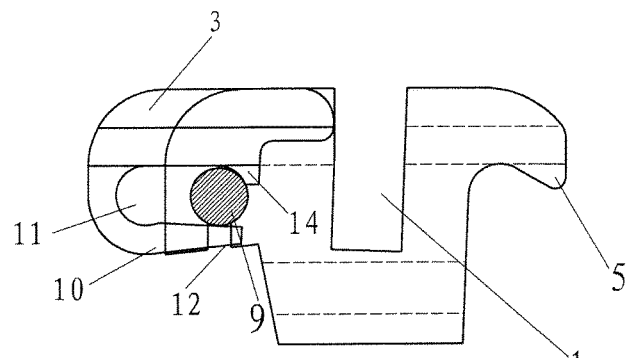
FIG. 15 is the schematic diagram of the open status of the deformation 3 of the bracket cover in embodiment 1.

The deformation 3 of the bracket cover in embodiment 1, as shown in FIG. 14 and FIG. 15, the hook 10 is slantwise arranged towards the bottom surface 300 of the bracket cover 3, and the size of the clamping slot 11 of the hook is gradually reduced from inside to outside; the pin shaft 9 is clamped into the maximum place of the clamping slot 11 when the bracket cover is closed, and as shown in FIG. 15, the pin shaft 9 is arranged at the place which is near to the free end 12 of the hook and makes the hook 10 to be deformed when the bracket cover 3 is opened. After the structure is adopted, the hook can be made to be thin, i.e. a thin elastic reed, and the bottom of the clamping slot of the hook is always contacted with the pin shaft whatever the bracket cover slides, so that the bracket cover is convenient to lock. The structure has the benefit effect that the size error of the clamping slot in the bracket cover can be amplified, so that the bracket is more convenient to manufacture.

Figure 16:
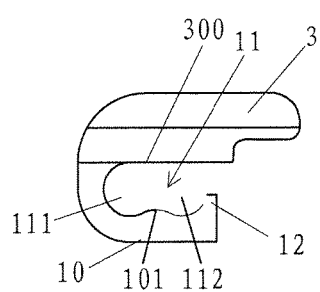
FIG. 16 is the structure schematic diagram of the deformation 4 of the bracket cover in embodiment 1.

The deformation 4 of the bracket cover in embodiment 1: similarly, the hook 10 is lengthened to prevent the pin shaft 9 from departing from the hook 10 at the beginning design time, as shown in FIG. 16, an arc lug boss 101 is arranged in the middle of the clamping slot 11 of the hook 10, and the clamping slot 11 is divided into a left clamping slot 111 and a right slot 112, which can be in clamping fit with the pin shaft respectively, by the arc lug boss 101.

Figure 17:
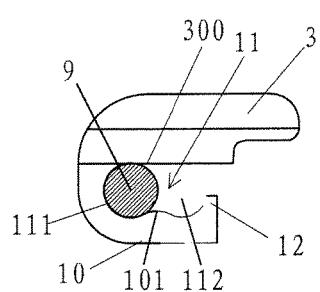
FIG. 17 is the schematic diagram of the match between the deformation 4 of the bracket cover and the pin shaft under the status that the bracket cover is closed in embodiment 1.
Figure 18:
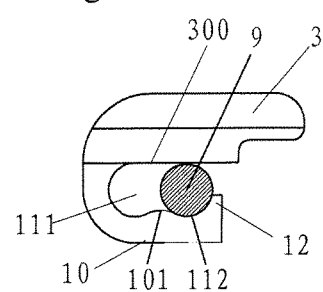
FIG. 18 is the schematic diagram of the match between the deformation 4 of the bracket cover and the pin shaft under the status that the bracket cover is opened in embodiment 1.

When the bracket cover 3 is rightwards pushed, as shown in FIG. 17, the pin shaft 9 is clamped into the left clamping slot 111 of the hook 10, the hook 10 is positioned with the pin shaft 9 through the arc lug boss 101 in a clamping way, the right end of the bracket cover 3 covers the arch wire bracket slot, and the bracket cover is locked in a closing way;

when the bracket cover 3 is leftwards pushed, as shown in FIG. 18, the pin shaft is clamped into the right clamping slot 112 of the hook 10, and the right end of the bracket cover departs from the arch wire bracket slot as well, so that the arch wire bracket slot can be exposed, the arch wire can be taken in or out, and the bracket cover is opened.

Figure 19:
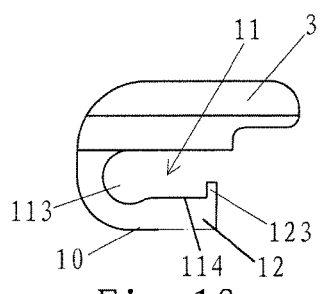
FIG. 19 is the structure schematic diagram of the deformation 5 of the bracket cover in embodiment 1.
Figure 20:
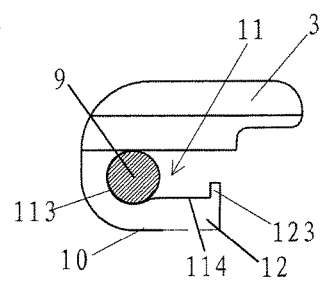
FIG. 20 is the schematic diagram of the match between the deformation 5 of the bracket cover and the pin shaft under the status that the bracket cover is closed in embodiment 1.

The deformation 5 of the bracket cover in embodiment 1: the difference between the deformation 5 and the deformation 4 is as follows, as shown in FIG. 19 and FIG. 20, the clamping slot 11 is divided into two sections, the left section is an arc slot 113, the right section is a straight slot 114, and the lowest point at the lower end of the pin shaft 9 and the bottom of the arc slot 113 are lower than the bottom of the straight slot 114; the free end 12 of the hook is provided with the stop block 123 for preventing the pin shaft 9 from departing from the hook.

Figure 21:
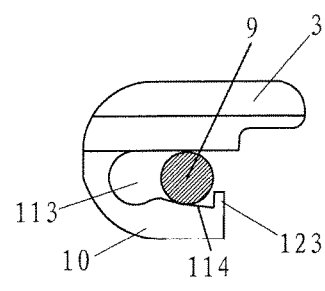
FIG. 21 is the schematic diagram of the match between the deformation 5 of the bracket cover and the pin shaft under the status that the bracket cover is opened in embodiment 1.
Figure 22:
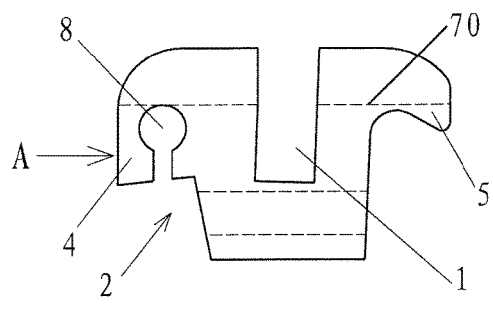
FIG. 22 is the structure schematic diagram of the bracket body in embodiment 2.
Figure 23:
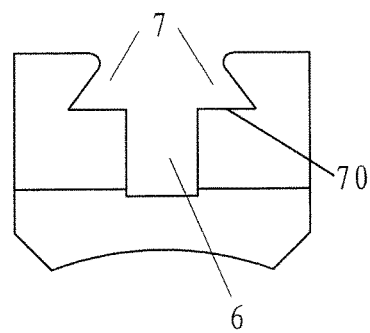
FIG. 23 is the auxiliary view A of FIG. 22.
Figure 24:
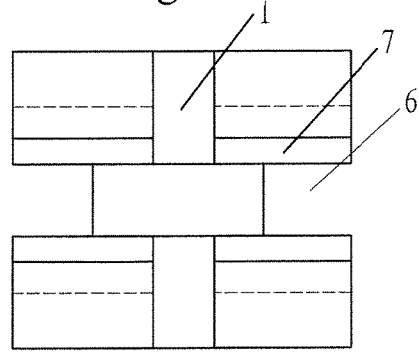
FIG. 24 is the top plan structure schematic diagram of FIG. 22.
Figure 25:
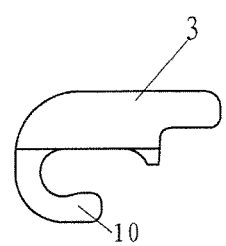
FIG. 25 is the structure schematic diagram of the bracket cover in embodiment 2.
Figure 26:
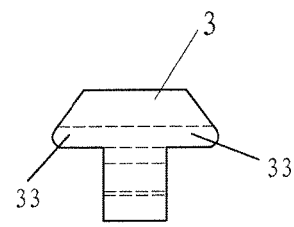
FIG. 26 is the side view of FIG. 25.
Figure 27:
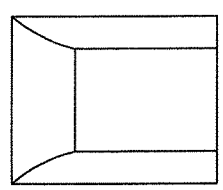
FIG. 27 is the structure schematic diagram of the vertical status of FIG. 25.
Figure 28:
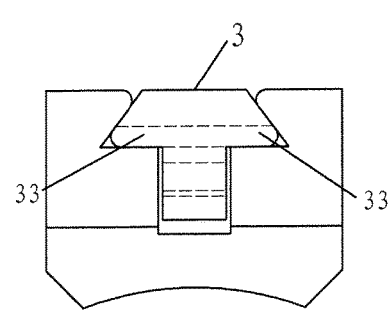
FIG. 28 is the schematic diagram of the sliding fit status between the bracket cover and the sliding chutes in embodiment 2.
Figure 29:
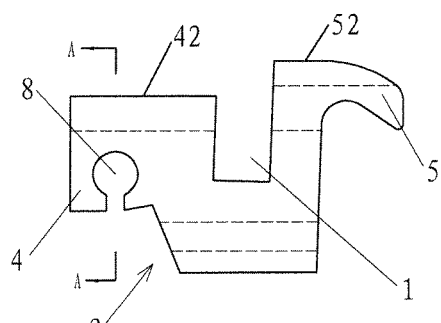
FIG. 29 is the structure schematic diagram of the bracket body in embodiment 3.

When the bracket cover is rightwards pushed, as shown in FIG. 20, the pin shaft 9 is clamped into the arc slot 113, the right end of the bracket cover covers the arch wire bracket slot, and the bracket cover is locked in a closing way;

when the bracket cover is leftwards pushed, as shown in FIG. 21, the pin shaft 9 departs from the arc slot 113, enters into the straight slot 114, and makes the hook 10 to be deformed, and the right end of the bracket cover departs from the arch wire bracket slot as well, so that the arch wire bracket slot can be exposed, the arch wire can be taken in or out, and the bracket cover is opened.

Embodiment 2 the embodiment focuses on the deformation of the sliding fit mode between the bracket cover and the bracket body, being different from the structure that the sliding chutes are the square chutes in embodiment 1, as shown in FIG. 22-FIG. 28, the sliding chutes 7 arranged at two sides of the bracket opening 7 are integrated into a dovetail groove, two sides of the bracket cover 3 are provided with the swallow-tail sliding blocks 33 of which the shapes and the sizes are matched with those of the dovetail groove, and two sides of the bracket cover 3 are clamped into the sliding chutes 7 and slide along with the sliding chutes 7. In the present invention, the highest point of the shaft hole 8 is lower than the plane where the bottoms 70 of the sliding chutes are placed.

Figure 30:
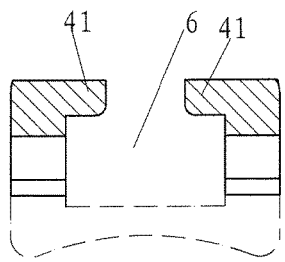
FIG. 30 is the A-A section view of FIG. 29.
Figure 31:
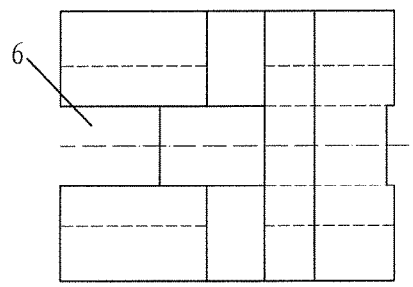
FIG. 31 is the top plan structure schematic diagram of FIG. 29.
Figure 32:
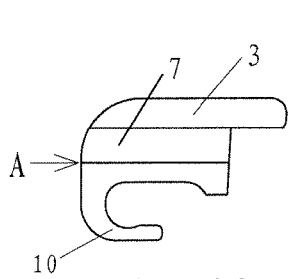
FIG. 32 is the structure schematic diagram of the bracket cover in embodiment 3.
Figure 33:
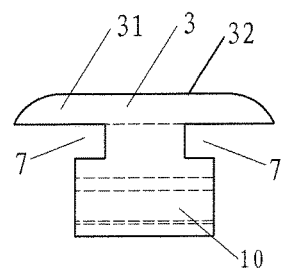
FIG. 33 is the auxiliary view A of FIG. 32.
Figure 34:
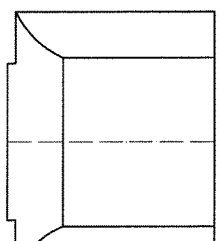
FIG. 34 is the structure schematic diagram of the vertical status of FIG. 32.
Figure 36:
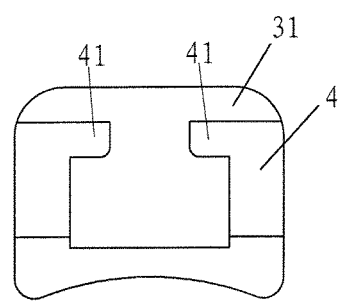
FIG. 36 is the auxiliary view A of FIG. 35.
Figure 37:
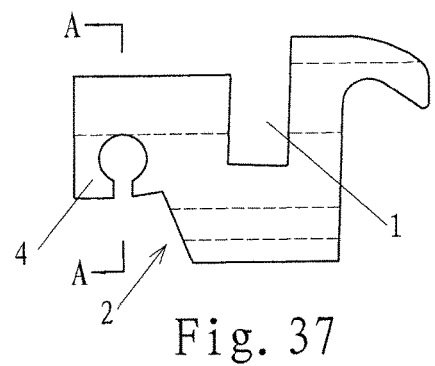
FIG. 37 is the structure schematic diagram of the bracket body in embodiment 4.
Figure 38:
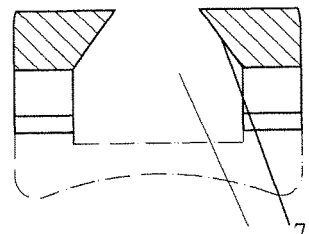
FIG. 38 is the A-A section view of FIG. 37.
Figure 39:
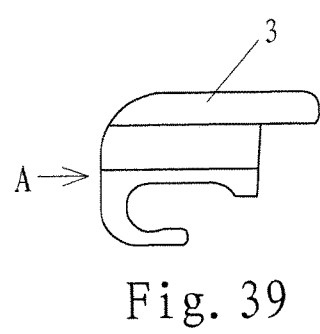
FIG. 39 is the structure schematic diagram of the bracket cover in embodiment 4.
Figure 40:
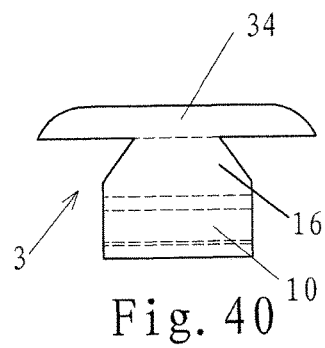
FIG. 40 is the auxiliary view A of FIG. 39.
Figure 41:
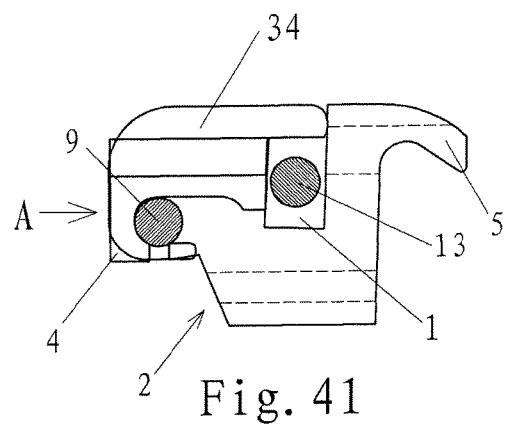
FIG. 41 is the schematic diagram of the close status of the bracket cover in embodiment 4.
Figure 42:
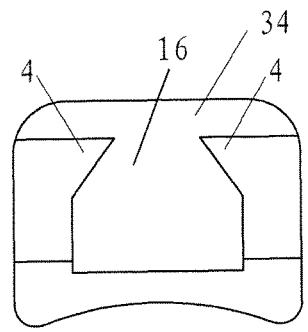
FIG. 42 is the auxiliary view A of FIG. 41.

Embodiment 3 as shown in FIG. 29-FIG. 36, as the other deformation of the sliding fit mode between the bracket cover and the bracket body, as shown in FIG. 32-FIG. 33, the bracket cover 3 has the shape of "I" integrally, two sides of the bracket cover 3 are symmetrically provided with the concave sliding chutes 7. As shown in FIG. 30, the bracket opening 6 is narrow in the upper part and wide in the lower part, two sides of the upper part of the bracket opening 6 are symmetrically provided with two sliding rails 41 which extend towards the middle of the bracket opening 6, after the bracket cover 3 is inserted into the bracket opening 6, the sliding rails 41 are clamped into the sliding chutes 7, the sliding rails 41 are in sliding fit with the sliding chutes 7, and the upper part 31 of the bracket cover covers on the arch wire bracket slot 1 and the work wing 4 at the left side of the arch wire bracket slot.

Figure 35:
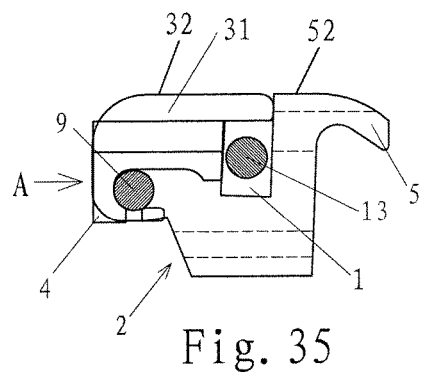
FIG. 35 is the schematic diagram of the close status of the bracket cover in embodiment 3.

The upper surface 42 of the work wing 4 at the left side of the arch wire bracket slot is lower than the upper surface 52 of the work wing 5 at the right side of the arch wire bracket slot, and when the upper part 31 of the bracket cover covers on the work wing 4 at the left side of the arch wire bracket slot, as shown in FIG. 35, the upper surface 32 of the bracket cover 3 is in parallel with the upper surface 52 of the work wing 5 at the right side of the arch wire bracket slot.

Embodiment 4 being different from embodiment 3, as shown in FIG. 37-FIG. 42, the bracket opening 6 is a swallow-tail sliding chute 7 integrally, similarly, the bracket opening 6 is narrow in the upper part and wide in the lower part, the bracket cover 3 comprises a bracket cover body 34 and sliding blocks 16 arranged under the bracket cover body 34 to be matched with the swallow-tail sliding chute 7, after the bracket cover 3 is inserted into the bracket opening 6, the sliding blocks 16 are in sliding fit with the swallow-tail sliding chute 7, and the bracket cover body 34 covers on the arch wire bracket slot 1 and the work wing 4 at the left side of the arch wire bracket slot 1.

The upper end of the bracket cover covers on the work wing at the left side of the arc wire bracket slot in embodiment 3 and embodiment 4, and the structure design has the greatest advantage: in the case that the height of the bracket is not heightened, the upper end of the bracket cover is configured to completely cover the arc wire bracket slot and the bracket body at the left side of the arc wire bracket slot, and the upper end of the bracket body at the right side of the arc wire bracket slot is sealed and is in parallel with the upper surface of the bracket cover, so that the whole upper surface of the bracket is integrated and covers all the slots, therefore, the cleanliness and the aesthetics of the bracket can be greatly improved.

Embodiment 5 the embodiment focuses on the difference between the structure form of the elastic element in embodiment 5 and that in embodiment 1, an orthodontic self-locking bracket of the embodiment 5, as shown in FIG. 43-FIG. 51, comprising a bracket body 2 having an arch wire bracket slot 1 and a bracket cover 3 matched with the bracket body 2, wherein two sides of the arch wire bracket slot 1 are respectively provided with work wings 4 and 5, a bracket opening 6 is arranged at the intersection of the arch wire bracket slot 1 on the bracket body 2, two sides of the bracket opening 6 are symmetrically provided with a sliding chute 7 respectively formed by means of linear cutting, the bracket cover 3 is arranged within the sliding chutes 7 in a sliding way, the work wing 4 at the left side of the arch wire bracket slot 1 is provided with a shaft hole 8, the shaft hole 8 is intercrossed with the bracket opening 6 and penetrates through the bracket body 2, the shaft hole 8 is internally provided with a pin shaft 9 which penetrates through the bracket opening 6, and the upper end of the shaft hole 8 is not higher than the bottom surfaces 70 of the sliding chutes 7.

As shown in FIG. 44 and FIG. 50, the sliding chutes 7 at two sides of the bracket opening are the square chutes, two ends of the bracket cover 3 are symmetrically provided with sliding blocks 16 of which the shapes and the sizes are matched with the those of the square chutes, and the sliding blocks 16 are clamped into the sliding chutes 7 and slide along with the sliding chutes 7.

As shown in FIG. 47-FIG. 48, the bracket cover 3 is provided with an elastic element which is in clamping fit with the pin shaft 9, specifically, the lower part of the bracket cover 3 is provided with a convex block 35, the convex block 35 is arranged in the middle at the bottom surface of the bracket cover 3, the convex block 35 is inserted into the bracket opening 6, the bottom surface 300 of the convex block 35 or the bracket cover 3 are concavely provided with a clamping slot 11 matched with the pin shaft 9, the elastic element is a shrapnel 36 which is deformable after being stressed above the clamping slot 11, the shrapnel 36 is arranged within the convex block 35, and the upper end of the pin shaft 9 is arranged within the clamping slot 11 and is in contacting fit with the shrapnel 36.

It should be noted that, the part of the right end of the bracket cover 3, which is used for covering the arch wire bracket slot 1, is configured into a thin and flat cover body 301, therefore, the arc wire placing space can be enlarged, and the height of the bracket body can be reduced.

As shown in FIG. 46, the clamping slot 11 is an arc slot integrally, a flange 29 downwards extends out of the middle of the arc slot, and the lower end of the flange 29 is higher than the bottom surface 300 of the bracket cover, i.e. the lower end of the flange 29 can not exceed the bottom surface 300 of the bracket cover; the flange 29 is arc integrally, the arc slot is divided into a left arc slot 117 and a right arc slot 118, which can be in clamping fit with the pin shaft respectively, by the flange 29.

As shown in FIG. 49, when the bracket cover 3 is rightwards pushed, the upper end of the pin shaft 9 is clamped into the left arc slot 117 of the bracket cover, and the bracket cover is locked in a closing way.

As shown in FIG. 51, when the bracket cover 3 is leftwards pushed, the arc slot 117 of the bracket cover departs from the pin shaft 9, the pin shaft 9 makes the shrapnel 33 to be deformed and clamped into the right arc slot 118 when passing through the flange 29, the right end of the bracket cover departs from the arch wire bracket slot 1 as well, and the bracket cover is opened.

The deformation 1 of embodiment 5: as the improvement of the bracket cover or the clamping slot in embodiment 5, as shown in FIG. 52, the clamping slot 11 is divided into two section, the left section is the arc slot 115 of which the bottom is arc, the right section is the straight slot 116 of which the bottom is horizontal, the highest point of the arc slot 115 is higher than the plane where the bottom of the straight slot 116 is placed, and the height of the plane where the bottom of the straight slot 116 is placed is lower than the highest point of the pin shaft 9 or the shaft hole 8; specifically, the shrapnel 36 is formed as follows, the bracket cover 3 is internally provided with a gap 24, the start point of the gap 24 is placed at the right end of the clamping slot 11, i.e. the right-most end of the straight slot 116, the end point of the gap 24 is placed above the arc slot 115, and the shrapnel 36 is formed at the part surrounded by the gap 24 and the clamping slot 11; from right to left, the gap 24 is arranged slantwise and upwards.

As shown in FIG. 53, the pin shaft 9 is immovable, when the bracket cover 3 is rightwards pushed, the pin shaft 9 is clamped into the arc slot 115 of the bracket cover 3, the right end of the bracket cover covers the arc wire bracket slot 1, and the bracket cover 3 is locked in a closing way.

As shown in FIG. 54, the pin shaft 9 is immovable, when the bracket cover 3 is leftwards pushed, the arc slot 115 of the bracket 3 departs from the pin shaft 9, the pin shaft 9 makes the shrapnel 36 to be deformed and clamped into the straight slot 116 of the bracket cover, and the right end of the bracket cover departs from the arch wire bracket slot as well, so that the arch wire bracket slot can be exposed, the arch wire can be taken in or out, and the bracket cover is opened.

The deformation 2 of the bracket cover in embodiment 5: as shown in FIG. 55, the clamping slot 11 is divided into two section, the left section is the arc slot 115 of which the bottom is arc, the right section is the straight slot 116 of which the bottom is horizontal, the highest point of the arc slot 115 is higher than the plane where the bottom of the straight slot 116 is placed, and the height of the plane where the bottom of the straight slot 116 is placed is lower than the highest point of the pin shaft; the bracket cover 3 is internally provided with a gap 24, the start point of the gap 24 is placed on the right side face 302 of the bracket cover 3, the end point of the gap 24 is placed above the arc slot 115, and the shrapnel 36 is formed between the gap 24 and the clamping slot 11;

As shown in FIG. 56, the pin shaft 9 is immovable, when the bracket cover 3 is rightwards pushed, the upper end of the pin shaft 9 is clamped into the arc slot 115 of the bracket cover, the right end of the bracket cover covers the arc wire bracket slot, and the bracket cover is locked in a closing way;

As shown in FIG. 57, the pin shaft 9 is immovable, when the bracket cover is leftwards pushed, the arc slot 115 of the bracket departs from the pin shaft 9, the pin shaft 9 makes the shrapnel 36 to be deformed and clamped into the straight slot of the bracket cover, and the right end of the bracket cover departs from the arch wire bracket slot as well, so that the arch wire bracket slot can be exposed, the arch wire can be taken in or out, and the bracket cover is opened.

The deformation 3 of the bracket cover in embodiment 5: as shown in FIG. 58, the clamping slot 11 is an arc slot integrally, a flange 29 downwards extends out of the middle of the arc slot, the lower end of the flange 29 is higher than the bottom surface 300 of the bracket cover, and the arc slot is divided into a left arc slot 117 and a right arc slot 118, which can be in clamping fit with the pin shaft respectively, by the flange 29; the bracket cover is internally provided with a gap 24, the start point of the gap 24 is placed on the right side face 302 of the bracket cover 3, the end point of the gap is placed above the left arc slot 117, and the shrapnel 36 is formed between the gap and the clamping slot; the gap 24 is linear, and the gap is in parallel with the bottom surface of the bracket cover basically.

As shown in FIG. 59, the pin shaft 9 is immovable, when the bracket cover is rightwards pushed, the upper end of the pin shaft 9 is clamped into the left arc slot 117 of the bracket cover, the right end of the bracket cover covers the arc wire bracket slot, and the bracket cover is locked in a closing way;

As shown in FIG. 60, when the bracket cover is leftwards pushed, the arc slot 117 of the bracket cover departs from the pin shaft 9, the pin shaft 9 makes the shrapnel 36 to be deformed and clamped into the right arc slot 118, and the right end of the bracket cover departs from the arch wire bracket slot as well, so that the arch wire bracket slot can be exposed, the arch wire can be taken in or out, and the bracket cover is opened.

The deformation 4 of the bracket cover in embodiment 5: as shown in FIG. 61, the clamping slot 11 is an arc slot integrally, a flange 29 downwards extends out of the middle of the arc slot, the lower end of the flange 29 is higher than the bottom surface of the bracket cover 3, and the arc slot is divided into a left arc slot 117 and a right arc slot 118, which can be in clamping fit with the pin shaft respectively, by the flange 29; the bracket cover 3 is internally provided with a kidney hole 43 cast by the powder metallurgic method, certainly, the kidney hole 43 can be further made by the other methods, the kidney hole 43 is placed right above the clamping slot 11, the shape of the kidney hole 43 is matched with that of the bottom of the clamping slot 11, and the shrapnel 33 is formed between the kidney hole 43 and the clamping slot 32.

As shown in FIG. 62 and FIG. 63, the bracket cover 3 is leftwards or rightwards pushed, and the pin shaft can make the shrapnel 36 to be deformed when passing through the flange 29, so that the pin shaft can be clamped into the left arc slot 117 or the right arc slot 118.

Figure 64:
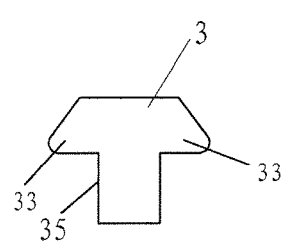
FIG. 64 is the structure schematic diagram of the side face of the bracket cover in embodiment 6.
Figure 65:
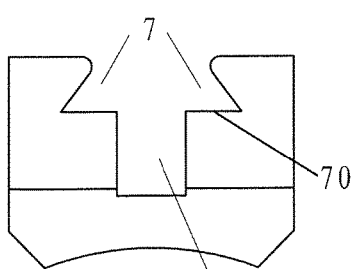
FIG. 65 is the structure schematic diagram of the sliding chutes of the bracket body in embodiment 6.
Figure 66:
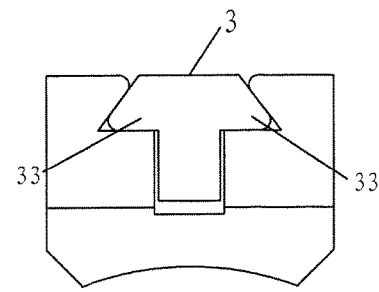
FIG. 66 is the schematic diagram of the sliding fit between the bracket cover and the sliding chutes in embodiment 6.
Figure 67:
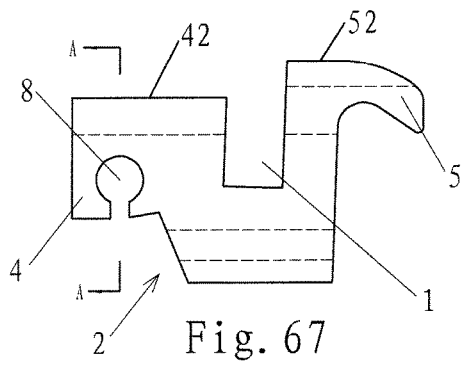
FIG. 67 is the structure schematic diagram of the bracket body in embodiment 7.

Embodiment 6 the embodiment focuses on the deformation of the sliding fit mode between the bracket cover and the bracket body, the form mode of the elastic element and the lock mode of the bracket cover in embodiment 6 are as the same as those in embodiment 5, but the structure that the sliding chutes are the square chutes in embodiment 6 is different from that in embodiment 5, as shown in FIG. 64-FIG. 66, the sliding chutes 7 arranged at two sides of the bracket opening 6 are integrated into a dovetail groove, two sides of the bracket cover 3 are provided with swallow-tail sliding blocks 33 of which the shapes and the sizes are matched with those of the dovetail groove, a convex block 35 is arranged under the swallow-tail sliding blocks 33, and two sides of the bracket cover 3 are clamped into the sliding chutes 7 and slide along with the sliding chutes 7. In the present invention, the highest point of the shaft hole 8 is lower than the plane where the bottoms 70 of the sliding chutes 7 are placed.

Figure 68:
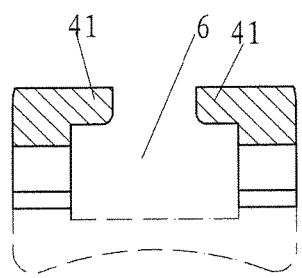
FIG. 68 is the A-A section view of FIG. 67.
Figure 69:
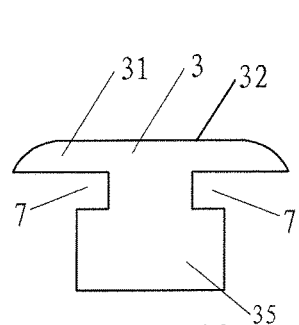
FIG. 69 is the structure schematic diagram of the side face of the bracket cover in embodiment 7.
Figure 70:
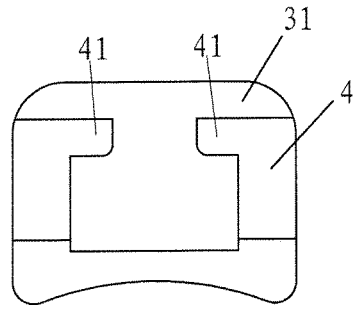
FIG. 70 is the schematic diagram of the sliding fit between the bracket cover and the sliding chutes in embodiment 7.

Embodiment 7 the embodiment focuses on the deformation of the sliding fit mode between the bracket cover and the bracket body, the form mode of the elastic element and the lock mode of the bracket cover in embodiment 7 are as the same as those in embodiment 5, and the structure that the sliding chutes are the square chutes in embodiment 7 is different from that in embodiment 5, as shown in FIG. 67-FIG. 71, as the other deformation of the sliding fit mode between the bracket cover and the bracket body, as shown in FIG. 69-FIG. 70, the bracket cover 3 has the shape of "I" integrally, two sides of the bracket cover 3 are symmetrically provided with the concave sliding chutes 7. As shown in FIG. 68, the bracket opening 6 is narrow in the upper part and wide in the lower part, two sides of the upper part of the bracket opening 6 are symmetrically provided with two sliding rails 41 which extend towards the middle of the bracket opening 6, after the bracket cover 3 is inserted into the bracket opening 6, the sliding rails 41 are clamped into the sliding chutes 7, the sliding rails 41 are in sliding fit with the sliding chutes 7, and the upper part 31 of the bracket cover covers on the arch wire bracket slot 1 and the work wing 4 at the left side of the arch wire bracket slot.

Figure 71:
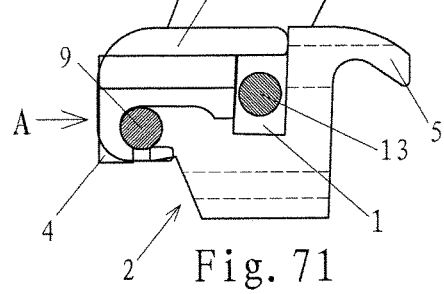
FIG. 71 is the schematic diagram of the lock status of the bracket cover within the bracket body in embodiment 7.
Figure 72:
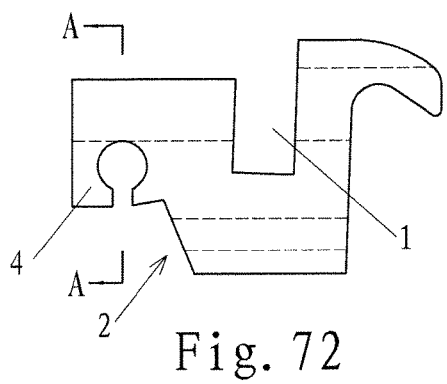
FIG. 72 is the structure schematic diagram of the bracket body in embodiment 8.
Figure 73:
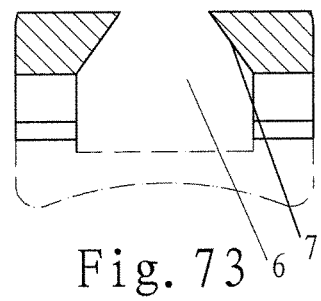
FIG. 73 is the A-A section view of FIG. 72.
Figure 74:
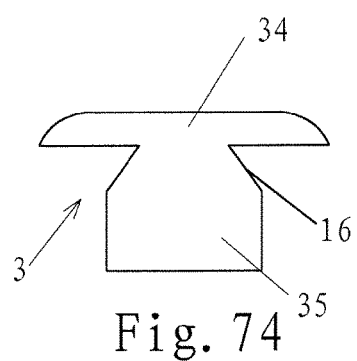
FIG. 74 is the structure schematic diagram of the side face of the bracket cover in embodiment 8.
Figure 75:
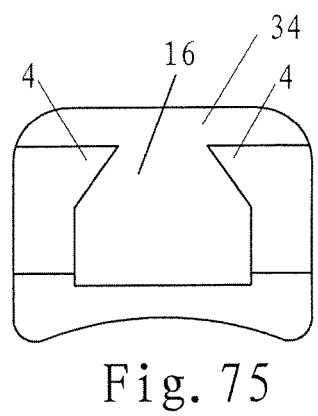
FIG. 75 is the schematic diagram of the sliding fit between the bracket cover and the sliding chutes in embodiment 8.
Figure 76:
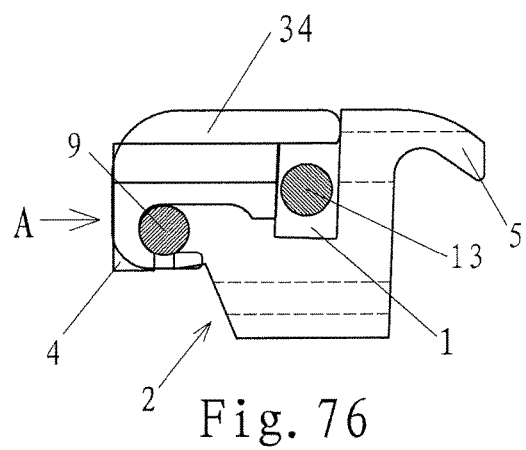
FIG. 76 is the schematic diagram of the lock status of the bracket cover within the bracket body in embodiment 8.

The upper surface 42 of the work wing 4 at the left side of the arch wire bracket slot is lower than the upper surface 52 of the work wing 5 at the right side of the arch wire bracket slot, and when the upper part 31 of the bracket cover covers on the work wing 4 at the left side of the arch wire bracket slot, as shown in FIG. 71, the upper surface 32 of the bracket cover 3 is in parallel with the upper surface 52 of the work wing 5 at the right side of the arch wire bracket slot.

Embodiment 8 being similar to but being different from embodiment 7, as shown in FIG. 72-FIG. 76, the bracket opening 6 is integrated into a swallow-tail sliding chute 7, similarly, the bracket opening 6 is narrow in the upper part and wide in the lower part, the bracket cover 3 comprises a bracket cover body 34 and sliding blocks 16 arranged under the bracket cover body 34 to be matched with the swallow-tail sliding chute 7, the convex block 35 is arranged under the sliding blocks 16, after the bracket cover 3 is inserted into the bracket opening 6, the sliding blocks 16 are in sliding fit with the swallow-tail sliding chute 7, and the bracket cover body 34 covers on the arch wire bracket slot 1 and the work wing 4 at the left side of the arch wire bracket slot 1.

The upper end of the bracket cover covers on the work wing at the left side of the arc wire bracket slot in embodiment 7 and embodiment 8, and the structure design has the greatest advantage: in the case that the height of the bracket is not heightened, the upper end of the bracket cover is configured to completely cover the arc wire bracket slot and the bracket body at the left side of the arc wire bracket slot, and the upper end of the bracket body at the right side of the arc wire bracket slot is sealed and is in parallel with the upper surface of the bracket cover, so that the whole upper surface of the bracket is integrated and covers all the slots, therefore, the cleanliness and the aesthetics of the bracket can be greatly improved.

The invention claimed is:

1. An orthodontic self-locking bracket, comprising a bracket body having an arch wire bracket slot and a bracket cover matched with the bracket body, wherein two sides of the arch wire bracket slot are provided with work wings, wherein a bracket opening is arranged at an intersection of the arch wire bracket slot on the bracket body, and the bracket cover is inserted into the bracket opening and is in sliding fit with the bracket body; a left side of the arch wire bracket slot is provided with a pin shaft penetrating through the bracket opening, and the pin shaft is in clamping fit with a lower part of the bracket cover, so that the arch wire bracket slot can be closed and opened by the bracket cover; and wherein the bracket cover is provided with an elastic element which is deformable after being stressed, and a clamping slot which is in clamping fit with the pin shaft is arranged on the elastic element; the pin shaft makes the elastic element to be deformed and to be in clamping fit with different positions of the clamping slot when the bracket cover slides, and a right end of the bracket cover covers or departs from the arch wire bracket slot.

2. The orthodontic self-locking bracket according to claim 1, wherein: two sides of the bracket opening are symmetrically provided with a sliding chute respectively, and the bracket cover is arranged within the sliding chutes.

3. The orthodontic self-locking bracket according to claim 2, wherein:
the sliding chutes arranged at two sides of the bracket opening are integrated into a dovetail groove, a longitudinal section of the bracket cover has a shape of swallow tail, and two sides of the bracket cover are clamped into the sliding chutes and slide along therewith;
or wherein:
the sliding chutes arranged at two sides of the bracket opening are square chutes, two ends of the bracket cover are symmetrically provided with sliding blocks of which the shapes and sizes are matched with those of the square chutes, and the sliding blocks are clamped into the sliding chutes and slide along therewith.

4. The orthodontic self-locking bracket according to claim 1, wherein: an upper part of the bracket cover covers on the work wing at the left side of the arch wire bracket slot, and a sliding rail face matched with the bracket cover is formed on an upper end of the work wing at the left side of the arch wire bracket slot.

5. The orthodontic self-locking bracket according to claim 4, wherein: the bracket cover has a shape of "I" integrally, two sides of the bracket cover are symmetrically provided with concave sliding chutes, the bracket opening is narrow in its upper part and wide in its lower part, two sides of the upper part of the bracket opening are symmetrically provided with two sliding rails, after the bracket cover is inserted into the bracket opening, the sliding rails are in sliding fit with the sliding chutes, and the upper part of the bracket cover covers on the arch wire bracket slot and the work wing at the left side of the arch wire bracket slot.

6. The orthodontic self-locking bracket according to claim 4, wherein: the bracket opening is a swallow-tail shaped sliding chute integrally, the bracket cover comprises a bracket cover body and sliding blocks arranged under the bracket cover body to be matched with the swallow-tail shaped sliding chute, after the bracket cover is inserted into the bracket opening, the sliding blocks are in sliding fit with the swallow-tail shaped sliding chute, and the bracket body cover covers on the arch wire bracket slot and the work wing at the left side of the arch wire bracket slot.

7. The orthodontic self-locking bracket according to claim 1, wherein: the elastic element is a hook which is deformable after being stressed at one end of the bracket cover in a bending way, the hook is inserted into the bracket opening, and the hook is internally provided with the clamping slot; the bracket cover slides left and right, so that the right end of the bracket cover covers or departs from the arch wire bracket slot, and the hook is matched with the pin shaft, so that the bracket cover can be opened and closed.

8. The orthodontic self-locking bracket according to claim 7, wherein: the clamping slot of the hook is an arc slot, a free end of the hook tilts to form into a lug boss which is in clamping fit with the pin shaft, the pin shaft is clamped into the clamping slot of the hook and is limited by the lug boss when the bracket cover is closed, the lug boss engages against the pin shaft and makes the hook to be deformed when the bracket cover is opened.

9. The orthodontic self-locking bracket according to claim 7, wherein: the shape and the size of the clamping slot of the hook are matched with those of the cross section of the pin shaft; and a free end of the hook is tilted to form into the lug boss which is in clamping fit with the pin shaft.

10. The orthodontic self-locking bracket according to claim 7, wherein:
the hook is formed by one end of the bracket cover that is bent towards a bottom surface of the bracket cover at 180 degrees, the length of the hook is lengthened, so that the pin shaft cannot slide out of the clamping slot, the clamping slot of the hook comprises an internal clamping slot which departs from the free end of the hook and an external clamping slot which is near to the free end of the hook, the shape and the size of the internal clamping slot are matched with those of the cross section of the pin shaft, and the height of the external clamping slot is less than the diameter of the pin shaft or the lower end face of the external clamping slot is higher than the lower end of the pin shaft;
the pin shaft is clamped into the internal clamping slot when the bracket cover is closed, and the pin shaft is arranged within the external clamping slot and makes the hook to be deformed when the bracket cover is opened;
or wherein:
the hook is slantwise arranged towards the bottom surface of the bracket cover, and the size of the clamping slot of the hook is gradually reduced from inside to outside; the pin shaft is clamped into a maximum place of the clamping slot when the bracket cover is closed, and the pin shaft is arranged at the place which is near to the free end of the hook and makes the hook to be deformed when the bracket cover is opened.

11. The orthodontic self-locking bracket according to claim 7, wherein:
an arc lug boss is arranged in the middle of the clamping slot of the hook, and the clamping slot is divided into a left clamping slot and a right clamping slot, which can be in clamping fit with the pin shaft respectively, by the arc lug boss;
when the bracket cover is rightwards pushed, the pin shaft is clamped into the left clamping slot of the hook, the hook is positioned with the pin shaft in a clamping way, the right end of the bracket cover covers the arch wire bracket slot, and the bracket cover is locked in a closing way;
when the bracket cover is leftwards pushed, the pin shaft is clamped into the right clamping slot of the hook, and the right end of the bracket cover departs from the arch wire bracket slot as well, so that the arch wire bracket slot can be exposed, the arch wire can be taken in or out, and the bracket cover is opened;
or wherein:
the clamping slot is divided into two sections, a left section is an arc slot, a right section is a straight slot, and a lowest point at the lower end of the pin shaft and the bottom of the arc slot are lower than the bottom of the straight slot;
when the bracket cover is rightwards pushed, the pin shaft is clamped into the arc slot, the right end of the bracket cover covers the arch wire bracket slot, and the bracket cover is locked in a closing way;
when the bracket cover is leftwards pushed, the pin shaft departs from the arc slot, enters into the straight slot, and makes the hook to be deformed, and the right end of the bracket cover departs from the arch wire bracket slot as well, so that the arch wire bracket slot can be exposed, the arch wire can be taken in or out, and the bracket cover is opened.

12. The orthodontic self-locking bracket according to claim 7, wherein: a stop block used for stopping the pin shaft to prevent the bracket cover from sliding out of the bracket body is arranged on a bottom surface of the bracket cover, and the stop block is arranged within the bracket opening.

13. The orthodontic self-locking bracket according to claim 7, wherein: the part of the right end of the bracket cover, which is used for covering the arch wire bracket slot, is configured into a thin and flat cover body.

14. The orthodontic self-locking bracket according to claim 1, wherein: the clamping slot is concavely arranged on a bottom surface of the bracket cover, the elastic element is a shrapnel which is deformable after being stressed above the clamping slot, and the upper end of the pin shaft is arranged within the clamping slot and is in contacting fit with the shrapnel.

15. The orthodontic self-locking bracket according to claim 14, wherein:
the clamping slot is divided into two sections, the left section is the arc slot, the right section is the straight slot, the highest point of the arc slot is higher than the plane where the bottom of the straight slot is placed, and the height of the plane where the bottom of the straight slot is placed is lower than the highest point of the pin shaft; the bracket cover is internally provided with a gap, the start point of the gap is placed at the right end of the clamping slot, the end point of the gap is placed above the arc slot, from right to left, the gap is arranged upwards and slantwise; and the shrapnel is formed at the part surrounded by the gap and the clamping slot;
when the bracket cover is rightwards pushed, the upper end of the pin shaft is clamped into the arc slot of the bracket cover, the right end of the bracket cover covers the arch wire bracket slot, and the bracket cover is locked in a closing way;

when the bracket cover is leftwards pushed, the arc slot of the bracket cover departs from the pin shaft, the pin shaft makes the shrapnel to be deformed and clamped into the straight slot of the bracket cover, and the right end of the bracket cover departs from the arch wire bracket slot as well, so that the arch wire bracket slot can be exposed, the arch wire can be taken in or out, and the bracket cover is opened;

or wherein:

the clamping slot is an arc slot integrally, a flange downwards extends out of the middle of the arc slot, the lower end of the flange is higher than the bottom surface of the bracket cover, and the arc slot is divided into a left arc slot and a right arc slot, which can be in clamping fit with the pin shaft respectively, by the flange; the bracket cover is internally provided with a gap, the start end of the gap is placed at the right end of the clamping slot, the end point of the gap is placed above the left arc slot, from right to left, the gap is arranged upwards and slantwise; and the shrapnel is formed at the part surrounded by the gap and the clamping slot;

when the bracket cover is rightwards pushed, the upper end of the pin shaft is clamped into the left arc slot of the bracket cover, the right end of the bracket cover covers the arch wire bracket slot, and the bracket cover is locked in a closing way;

when the bracket cover is leftwards pushed, the left arc slot of the bracket cover departs from the pin shaft, the pin shaft makes the shrapnel to be deformed and clamped into the right arc slot of the bracket cover, and the right end of the bracket cover departs from the arch wire bracket slot as well, so that the arch wire bracket slot can be exposed, the arch wire can be taken in or out, and the bracket cover is opened.

16. The orthodontic self-locking bracket according to claim 14, wherein: the clamping slot is an arc slot integrally, a flange downwards extends out of the middle of the arc slot, the lower end of the flange is higher than the bottom surface of the bracket cover, and the arc slot is divided into a left arc slot and a right arc slot, which can be in clamping fit with the pin shaft respectively, by the flange; the bracket cover is internally provided with a kidney hole, the kidney hole is arranged above the clamping slot, and the shrapnel is formed between the kidney hole and the clamping slot; the shape of the kidney hole is matched with that of the bottom of the clamping slot;

when the bracket cover is rightwards pushed, the upper end of the pin shaft is clamped into the left arc slot of the bracket cover, the right end of the bracket cover covers the arch wire bracket slot, and the bracket cover is locked in a closing way;

when the bracket cover is leftwards pushed, the left arc slot of the bracket cover departs from the pin shaft, the pin shaft makes the shrapnel to be deformed and clamped into the right arc slot, and the right end of the bracket cover departs from the arch wire bracket slot as well, so that the arch wire bracket slot can be exposed, the arch wire can be taken in or out, and the bracket cover is opened.

17. The orthodontic self-locking bracket according to claim 14, wherein: the lower part of the bracket cover is provided with a convex block, the convex block is inserted into a bracket opening, the clamping slot is arranged on the bottom surface of the convex block, and the shrapnel is arranged within the convex block.

18. The orthodontic self-locking bracket according to claim 1, wherein: the work wing at the left side of the arch wire bracket slot is provided with a shaft hole, the shaft hole is intercrossed with the bracket opening and penetrates through the bracket body, and the pin shaft penetrates in to the shaft hole and penetrates through the bracket opening.

* * * * *